(12) United States Patent
Brückner et al.

(10) Patent No.: US 10,765,855 B2
(45) Date of Patent: Sep. 8, 2020

(54) BREAKER DEVICE FOR ACTING ONTO A CLOSURE ELEMENT OF A MEDICAL TUBING

(71) Applicant: Fresenius Kabi Deutschland GmbH, Bad Homburg (DE)

(72) Inventors: Thomas Brückner, Mömbris (DE); Christian Hennecke, Westerfeld (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 392 days.

(21) Appl. No.: 15/759,012

(22) PCT Filed: Aug. 1, 2016

(86) PCT No.: PCT/EP2016/068263
§ 371 (c)(1),
(2) Date: Mar. 9, 2018

(87) PCT Pub. No.: WO2017/045825
PCT Pub. Date: Mar. 23, 2017

(65) Prior Publication Data
US 2019/0321620 A1      Oct. 24, 2019

(30) Foreign Application Priority Data

Sep. 14, 2015   (EP) ..................................... 15185069

(51) Int. Cl.
*F16K 31/02*       (2006.01)
*A61M 39/28*      (2006.01)
(Continued)

(52) U.S. Cl.
CPC .............. *A61M 39/281* (2013.01); *A61J 1/10* (2013.01); *A61M 2039/087* (2013.01);
(Continued)

(58) Field of Classification Search
CPC .............. A61M 39/281; A61M 39/221; A61M 2039/087; A61M 2039/222;
(Continued)

(56) References Cited

U.S. PATENT DOCUMENTS 2,659,253 A   11/1953 Myrick
3,266,287 A    8/1966 Gill
(Continued)

FOREIGN PATENT DOCUMENTS

DE       199 00 320 C1    7/2000
EP        0 235 591 A1    9/1987
(Continued)

OTHER PUBLICATIONS

International Search Report and Written Opinion, counterpart International Appl. No. PCT/EP2016/068263, dated Oct. 10, 2016 (9 pages).
(Continued)

*Primary Examiner* — Minh Q Le
(74) *Attorney, Agent, or Firm* — Cook Alex Ltd.

(57) ABSTRACT

A breaker device (1) for acting onto a closure element (40) of a medical tubing (4) comprises a drive arrangement (2) having an electric drive device (20) and a drive element (23) driven by the drive device (20), and a breaker module (3) which is arrangeable on the drive arrangement (2). The breaker module (3) comprises a housing (30), a movable part (31) movably arranged on the housing (30) and a breaking element (315) for acting onto the closure element (40) of the tubing (4), wherein the breaker module (3) in an attached state is placed on the drive arrangement (2), the drive element (23) being in operative connection with the movable part (31) in the attached state such that a movement of the drive element (23) causes the movable part (31) to move for actuating the breaking element (315). A control device (5)

(Continued)

serves for controlling the electric drive device (20) for driving the drive element (23). Herein, the control device (5) is constituted to control, during a detection routine, the electric drive device (20) to drive the drive element (23) in order to move the movable part (31), wherein the control device (5) is further constituted to analyse at least one feedback signal received during the detection routine for determining a type of the breaker module (3), the feedback signal being indicative of a movement of the movable part (31) during the detection routine.

20 Claims, 2 Drawing Sheets

(51) Int. Cl.
    *A61J 1/10*     (2006.01)
    *A61M 39/08*     (2006.01)
    *G05D 7/06*     (2006.01)

(52) U.S. Cl.
    CPC ......... *A61M 2205/103* (2013.01); *A61M 2205/3317* (2013.01); *A61M 2205/6036* (2013.01); *G05D 7/0617* (2013.01)

(58) Field of Classification Search
    CPC .... A61M 2205/103; A61M 2205/3317; A61M 2205/6036; A61J 1/10; G05D 7/0617
    USPC ......... 137/68.11, 487.5, 269; 251/349, 342; 225/103; 604/167.01, 403; 220/233; 81/3.2, 3.4
    See application file for complete search history.

(56) References Cited

U.S. PATENT DOCUMENTS

| | | | |
|---|---|---|---|
| 4,181,140 A | | 1/1980 | Bayham et al. |
| 4,294,247 A | | 10/1981 | Carter et al. |
| 4,340,049 A | | 7/1982 | Munsch |
| 4,386,622 A | | 6/1983 | Munsch |
| 4,510,825 A | | 4/1985 | Neron et al. |
| 4,586,928 A | | 5/1986 | Barnes et al. |
| 4,805,821 A | * | 2/1989 | Kowalczyk ............ B26F 3/002 225/103 |
| 5,330,464 A | * | 7/1994 | Mathias ............ A61M 39/221 604/403 |
| 5,427,145 A | | 6/1995 | Grabenkort |
| 5,709,685 A | | 1/1998 | Dombrowski et al. |
| 5,824,216 A | | 10/1998 | Joie et al. |
| 5,826,621 A | * | 10/1998 | Jemmott ........... A61M 5/16831 137/853 |
| 6,132,413 A | | 10/2000 | Mathias et al. |
| 6,156,025 A | | 12/2000 | Niedospial, Jr. et al. |
| 6,409,032 B1 | | 6/2002 | Bekkers et al. |
| 6,427,893 B1 | | 8/2002 | Penrod et al. |
| 6,470,780 B1 | | 10/2002 | Benuzzi |
| 6,491,659 B1 | | 12/2002 | Miyamoto |
| 9,192,756 B2 | | 11/2015 | Deverre et al. |
| 9,895,822 B2 | * | 2/2018 | Stonig ...................... B26F 3/00 |
| 2001/0039404 A1 | | 11/2001 | Rolle |
| 2003/0167893 A1 | | 9/2003 | Morris et al. |
| 2009/0227961 A1 | | 9/2009 | Meisberger et al. |
| 2010/0132512 A1 | | 6/2010 | Bucciaglia et al. |
| 2010/0269584 A1 | | 10/2010 | Horst |
| 2011/0198350 A1 | | 8/2011 | Meisberger et al. |
| 2013/0340836 A1 | | 12/2013 | Wambold |
| 2015/0306371 A1 | * | 10/2015 | Salo .................... A61M 39/221 225/1 |
| 2015/0367120 A1 | * | 12/2015 | Kusters ................. F16L 13/00 137/15.09 |
| 2018/0256884 A1 | * | 9/2018 | Bruckner ............ A61M 39/221 |

FOREIGN PATENT DOCUMENTS

| | | |
|---|---|---|
| WO | WO2004/058046 A2 | 7/2004 |
| WO | WO2006/114319 A1 | 11/2006 |
| WO | WO2010/065396 A1 | 6/2010 |
| WO | WO2012/080664 A2 | 6/2012 |
| WO | WO2012080664 A2 | 6/2012 |
| WO | WO2014/083412 A1 | 6/2014 |

OTHER PUBLICATIONS

YouTube video—https://www.youtube.com/watch?v=7u677isN1Og, published on Jul. 26, 2012, cited in U.S. Appl. No. 13/833,990 in Supplemental Information Disclosure Statement filed Jul. 8, 2016. A DVD was provided and assigned Artifact No. 13833990UA. The Artifact Sheet notification is attached.

European Search Report dated Mar. 4, 2014, for Application No. EP 13192157.9.

* cited by examiner

BREAKER DEVICE FOR ACTING ONTO A CLOSURE ELEMENT OF A MEDICAL TUBING

The invention relates to a breaker device for acting onto a closure element of a medical tubing according to the preamble of claim 1 and a method for operating a breaker device.

A breaker device of this kind, commonly referred to also as "breaking device" or "breaker", comprises a drive arrangement and a breaker module arrangeable on the drive arrangement. The drive arrangement comprises a drive device and a drive element driven by the drive device. The breaker module comprises housing, a movable part movably arranged on the housing and a breaking element for breaking acting onto the closure element of the tubing. In an attached state the breaker module is placed on the drive arrangement. In this attached state the drive element is in operative connection with the movable part such that a movement of the drive element causes the movable part to move for actuating the breaking element. The operation of the electric drive device is controlled by a control device.

The breaker module, in a modular fashion, can be arranged on the drive arrangement and, when it is attached to the drive arrangement, is functionally connected to the drive arrangement such that, via the drive device and the drive element of the drive arrangement, the movable part of the breaker module can be driven for actuating the breaking element. Via the breaking element a closure element of a medical tubing arranged on the breaker module can be opened such that a flow through the medical tubing becomes possible.

In medical tubing sets, for example within a blood bag system comprising one or multiple blood bags or other liquid containers, closure elements are placed within tubing sections in order to close a flowpath through the corresponding tubing. By closing one or multiple tubing sections of a tubing set, a blood bag system can for example be stored or transported. In order to prepare a blood component, for example for infusion purposes, a flowpath through a tubing from one container to another may then be opened by acting onto the closure element within the tubing.

Different systems of closure elements exist for closing a tubing and, hence, preventing a flow through the tubing. Closure elements generally have the shape of a cap or pin which is inserted into the lumen of a tubing such that the lumen of the tubing is closed off and a flow through the tubing is prevented. The different existing systems herein differ in the way the closure elements can be opened in order to allow a flow through the tubing.

In a first system, as for example described in WO 2004/058046 A2 or WO 2012/080664 A2, an opening of a flowpath can be achieved by breaking the closure element. In another system, as described for example in WO 2006/114319 A1, an opening of a flowpath can be achieved by deforming the closure element without actually breaking it. In both cases, the closure element even after opening remains in the tubing, but is broken or deformed such that a flow through the tubing is no longer prevented.

In principle, the opening of a closure element of this kind can be achieved manually by manually breaking or deforming the closure element within the tubing. For example, a closure element as described in WO 2012/080664 A2 can be broken by manually grabbing a tubing at the location of the closure element and by repeatedly bending it until the closure element breaks.

However, this may be a tedious task for a user such that there is a desire to provide an automatic opening device which can automatically open a closure element within a tubing.

Herein, because different systems of closure elements exist, one opening device may not be suitable to open different kinds of closure elements, because the different closure elements may require a different opening action. This may make it necessary to provide different opening devices for different closure elements, which however is costly and therefore to be avoided.

Instead of using multiple different opening devices, a breaker device of the type concerned herein may be used together with different breaker modules, the breaker modules having different configurations such that they are suitable to be used in connection with different closure elements, as for example described in WO 2014/083412 A1.

For this, the breaker module may be releasable from the drive arrangement by disengaging a locking mechanism of the breaker module from a locking element of the drive arrangement, such that one breaker module can be replaced by another.

Different breaker modules serving to act onto different closure elements of different tubings may have different designs and in particular, with their movable part, may be designed to perform different movement types. For example, the movable part may be guided on the housing of the breaker module to perform a longitudinal movement with respect to the housing when driven by the drive element, or it may be designed to perform a rotating or swivelling movement. Hence, different types of breaker modules exist which must be driven in different ways by means of the drive device of the drive arrangement.

Hence, when placing a specific breaker module on the drive arrangement in order to act onto a specific closure element within a tubing the control device must know what breaker module is placed on the drive arrangement such that the control device is enabled to control the drive device in a suitable manner.

Within current systems this is achieved by means of a manual configuration in that for example a service technician or a user manually adjusts a specific setting of the breaker device. According to the setting of the breaker device the control device then, during operation of the breaker device, controls the drive device such that the drive element is driven in an appropriate manner and the movable part is moved accordingly.

It is an object of the instant invention to provide a breaker device and a method for operating a breaker device which in an easy manner allow the controlling of a drive device in dependence of a type of a breaker module attached to a drive arrangement.

This object is achieved by means of a breaker device comprising the features of claim 1.

Accordingly, the control device is constituted to control, during a detection routine, the electric drive device to drive the drive element in order to move the movable part, wherein the control device is further constituted to analyse at least one feedback signal received during the detection routine for determining a type of the breaker module, the feedback signal being indicative of a movement of the movable part during the detection routine.

The control device hence is constituted to perform a detection routine, for example in a start-up phase prior to starting the normal operation of the breaker device. During this detection routine the control device controls the electric drive device of the drive arrangement to drive the drive element in order to move the movable part. During this movement at least one feedback signal is received which is indicative of the movement of the movable part and which may be analysed to determine which movement the movable part is designed to perform.

For example, by means of the feedback signal it may be recognized whether the movable part comes into abutment with a stop limiting the movement of the movable part. Additionally, a timing signal may be received indicating for example how long it takes to move the movable part until it comes into abutment with a stop. By recognizing in what way the movement of the movable part is limited by one or multiple stops and by monitoring for example how long it takes for the movable part to reach a stop, it for example is possible to determine within what boundaries a movement of the movable part is possible.

According to the information that is obtained about the movement of the movable part, it can then be determined what type of the breaker module has been attached to the drive arrangement, such that for the later operation of the drive arrangement a specific movement routine may be chosen for suitably driving the movable part.

Generally, different types of breaker modules may be attached to the drive arrangement, the breaker modules differing in the movement the movable part is designed to perform. For example, for a first design a movement of the movable part may not be limited by stops at all, such that the drive element of the drive arrangement may be continuously driven without ever reaching a stop. For a second design, however, the movement of the movable part may be limited by two stops in between which the movable part can be moved. A timing information herein may indicate the path length about which the movable part can be moved in between the associated stops.

The drive arrangement may for example comprise one or multiple detection devices for providing the feedback signals in dependence of a movement of the movable part. The detection devices herein may have a different constitution to provide different feedback signals indicative of the movement of the movable part.

For example, a first detection device may be constituted to monitor a motor current of the electric drive device. Hence, by means of the detection device the motor current of the drive device can be analysed in order to for example recognize whether the movable part is moved against a stop. This is based on the fact that the motor current will rise if the movable part comes into abutment with a stop (or generally experiences an increased mechanical resistance on its movement path), such that it can be recognized from the motor current if the movable part has reached an end of its movement path.

A second detection device may be constituted as a (micro-) mechanical switch which interacts with the movable part when the movable part is moved along its movement path. By means of a switch it for example can be recognized if the movable part approaches a stop or reaches a predefined position along its movement path. Because the movement paths of different types of breaker modules may differ, different mechanical switches may interact differently with the movable parts of different breaker modules, such that by means of mechanical switches it can be distinguished between different types of breaker modules.

For example, a first mechanical switch may interact with a movable part performing a longitudinal movement with respect to the housing of the breaker module when driven by the drive element, but may not interact with a movable part performing a swivelling movement with respect to the housing along a different movement path of a different breaker module. A second mechanical switch in turn may interact with a movable part performing a swivelling movement, but may not interact with a movable part which is longitudinally moved when driven by the drive element.

Other detection devices are conceivable for providing a feedback signal indicative of the movement of the movable part being driven by the drive element. Different feedback signals herein may be analysed separately or in combination in order to determine what type of breaker module has been arranged on the drive arrangement.

A predefined number of different types of breaker modules may exist, for example three different types of breaker modules designed to act onto three different types of closure elements. For a first type of breaker module for example no stops limiting the movement of the movable part are present. For a second type of breaker module two stops may be present in between which the movable part can be moved, and for a third type of breaker module likewise two stops may be present in between which the movable part can be moved. The second type of breaker module and the third type of breaker module herein may be distinguished from one another by different mechanical switches interacting with the breaker modules in different ways.

In another aspect, the drive element may be rotatable about an axis of rotation. The drive element may for example be rotatable with respect to a housing of the drive arrangement and is driven by the drive device of the drive arrangement to rotate about an axis of rotation.

The drive element may for example comprise one or multiple coupling elements to establish a positive-locking coupling with the movable part. The coupling element may for example be constituted by a pin protruding along the axis of rotation from a rotating body of the drive element. The pin herein beneficially is arranged eccentrically to the axis of rotation of the drive element such that it moves along a circular path about the axis of rotation when the drive element is rotated.

The coupling element of the drive element engages with a corresponding coupling mechanism of the movable part when the breaker module is arranged on the drive arrangement. The coupling mechanism of the movable part may for example be constituted by a groove or another engagement means into which the coupling element of the drive element may reach such that a movement of the drive element is transferred into a suitable movement of the movable part.

The movable part is coupled to the breaking element and, when moved, moves the breaking element such that the breaking element may perform a breaking motion for opening a closure element of a medical tubing arranged on the breaking element. The breaking element may for example have the shape of a fork into which the medical tubing may be inserted.

The movable part may for example be longitudinally guided on the housing such that, when driven by the drive element, the movable part is displaced with respect to the housing along a longitudinal movement direction. It is to be understood, however, that different breaker modules may have different movable parts which may perform a different kind of movement.

Depending on the type of the breaker module determined during the detection routine, the control device may, during normal operation, control the electric drive device to perform a particular predefined movement routine. The particular predefined movement routine herein may be chosen from a multiplicity of predefined movement routines stored in a storage of the control device, each movement routine being assigned to move the movable part in a predefined manner. For example, by means of a particular movement routine the drive element may be driven to move the movable part in between stops the movable part is associated with.

The object is also achieved by means of a method for operating a breaker device for acting onto a closure element of a medical tubing, the method comprising:

arranging a breaker module on a drive arrangement, the breaker module comprising a housing, a movable part movably arranged on the housing and a breaking element for acting onto the closure element of the tubing, wherein by arranging the breaker module on the drive arrangement the movable part is brought into operative connection with a drive element of the drive arrangement such that a movement of the drive element causes the movable part to move for actuating the breaking element, and a control device controls an electric drive device of the drive arrangement for driving the drive element.

Herein, the control device controls, during a detection routine, the electric drive device to drive the drive element in order to move the movable part, wherein the control device analyzes at least one feedback signal received during the detection routine for determining a type of the breaker module, the feedback signal being indicative of a movement of the movable part during the detection routine.

The advantages and advantageous embodiments described above for the breaker device equally apply also to the method, such that it shall be referred to the above.

The idea underlying the invention shall subsequently be described in more detail with respect to the embodiments shown in the figures. Herein:

Figure 1:
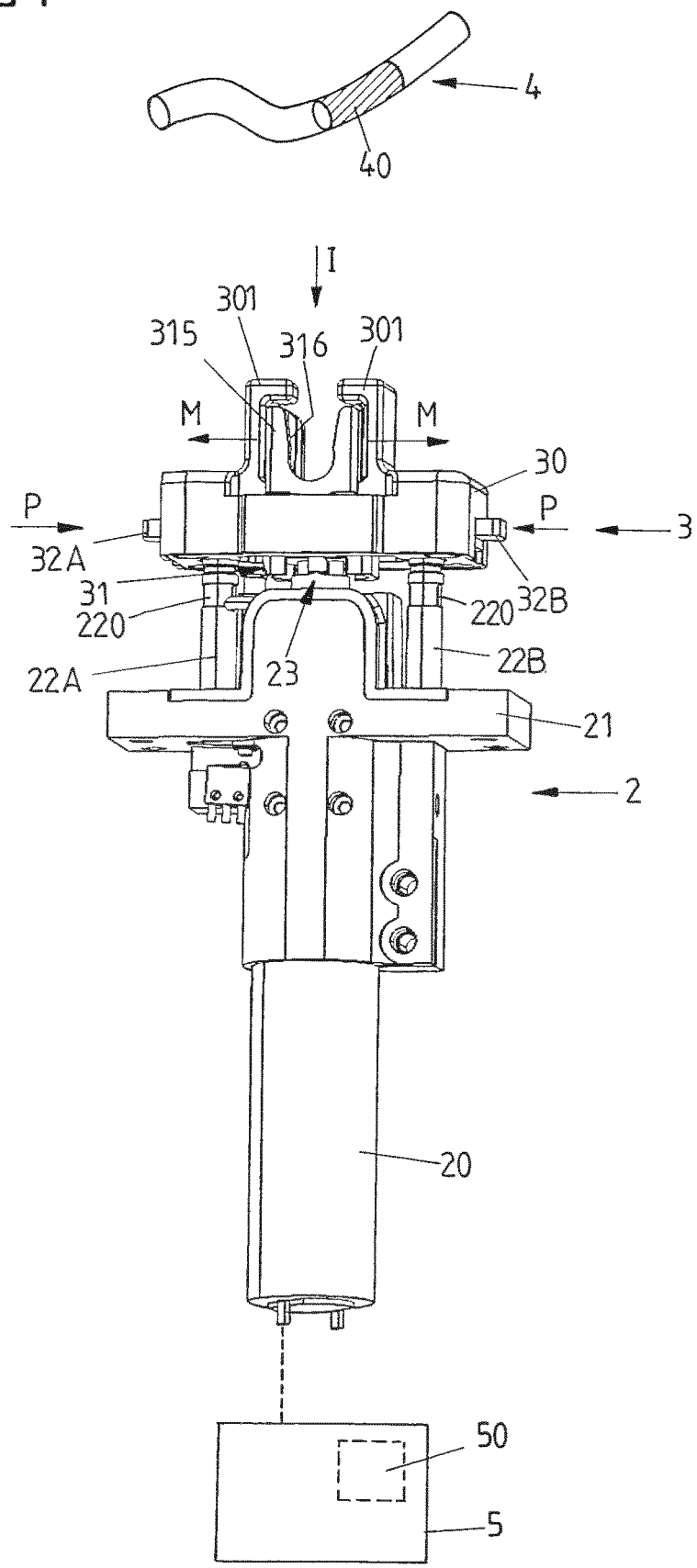
FIG. 1 shows a perspective view of a drive arrangement of a breaker device together with a breaker module.

FIG. 1 shows a breaker device 1 having a drive arrangement 2 and a breaker module 3.

Figure 2:
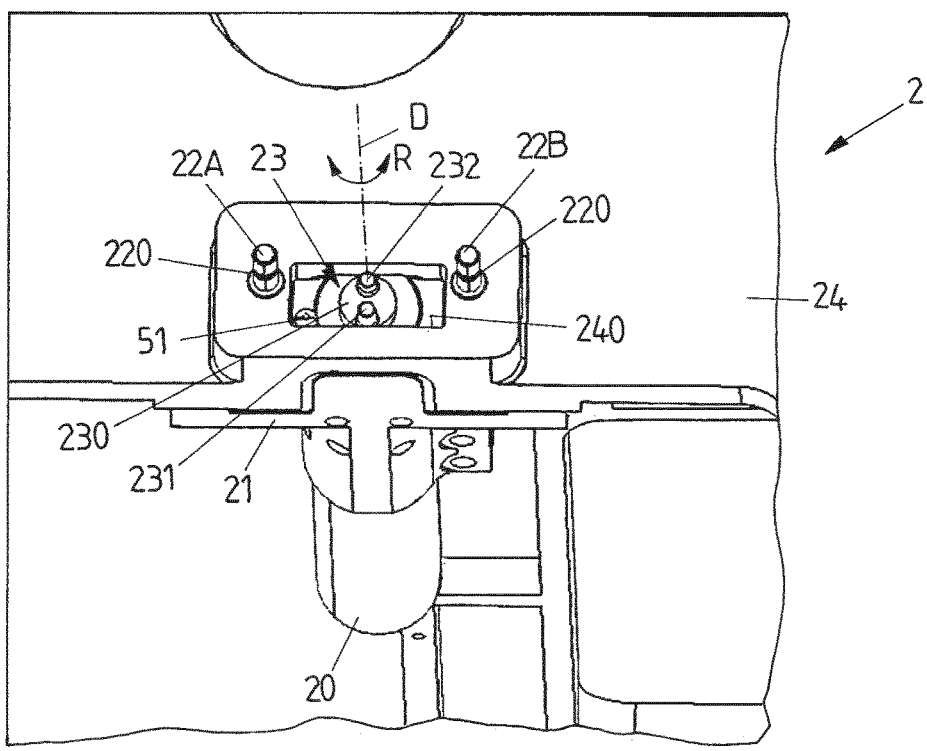
FIG. 2 shows a top view of the drive arrangement.

The drive arrangement 2 comprises an electric drive device 20 in the shape of an electric motor and a drive element 23 which, as visible in FIG. 2, is rotatable about a rotational axis D and comprises a rotating body 230 having a cylindrical shape and a pair of coupling elements 231, 232 in the shape of pins protruding from the body 230 along the axis of rotation D. The pins 231, 232 are arranged eccentrically to the axis of rotation D such that the pins 231, 232 move along a circular path along a rotation direction R about the axis of rotation D when the drive element 23 is driven by means of the electric drive device 20.

The drive arrangement 2 furthermore comprises a mounting element 21 on which the electric drive device 20 is mounted. Via the mounting element 21 the electric drive device 20 is connected to a housing element 24, as shown in FIG. 2.

The breaker device 1 may be part of a larger system such as a pump device, a centrifugation device or the like, the housing element 24 being part of the overall housing of the system.

As visible from FIGS. 1 and 2, a pair of locking elements 22A, 22B are arranged on the mounting element 21 and protrude from the mounting element 21 along the axis of rotation D. The locking elements 22A, 22B reach through the housing element 24 such that they are accessible from the outside, as visible in FIG. 2.

The locking elements 22A, 22B have the shape of pins and each comprise a circular groove 220. The locking elements 22A, 22B serve to establish a locking between the drive arrangement 2 and a breaker module 3 attached to the drive arrangement 2, as shall be described further below.

The drive element 23 is placed within an opening 240 of the housing element 24 such that it also is accessible from the outside. Via the drive element 23 an operative connection is established between a movable part 31 of the breaker module 3 and the electric drive device 20, as it also shall be described further below.

Figure 3:
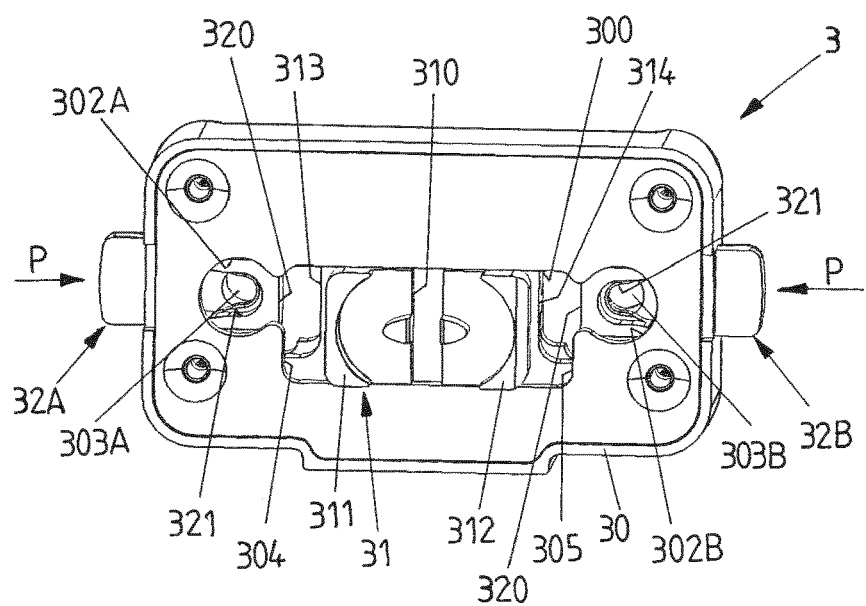
FIG. 3 shows a view of the breaker module from beneath.

The breaker module 3, as shown in FIG. 3, comprises a housing 30 having a longitudinal opening 300 at a bottom face facing the drive arrangement 2 when placing the breaker module 3 on the drive arrangement 2. Within the opening 300 the movable part 31 is placed such that the movable part 31 is guided on the housing 30 along a longitudinal movement direction.

The breaker module 3 furthermore comprises two actuation members 32A, 32B which are arranged on the housing 30 such that they can be displaced with respect to the housing 30 along a pushing direction P between a first, inner position and a second, outer position. The actuation members 32A, 32B have the shape of buttons and can be pushed into the housing 30 manually by a user by pressing onto the actuation members 32A, 32B.

The actuation members 32A, 32B are, in one embodiment, pretensioned towards their outer, second position such that, when released, they will assume there second, outer position (shown in FIG. 3).

The actuation members 32A, 32B serve a twofold function.

The actuation members 32A, 32B each comprise a head section 320, by which they can be brought into engagement with a corresponding engagement section 313, 314 in the shape of a recess on the movable part 31. Hence, when pushing the actuation members 32A, 32B in the pushing direction P into the housing 30, the head sections 320 engage with the engagement sections 313, 314 on opposite ends of the movable part 31 and in this way force the movable part 31 into a predefined, central position within the opening 300 of the housing 30. Hence, by pushing onto the actuation members 32A, 32B the movable part 31 is brought into a predefined position in which it can be coupled with the drive element 23 when the breaker module 3 is arranged on the drive arrangement 2.

For establishing the coupling with the drive arrangement 2 the movable part 31 comprises a groove 310 in which the pin 231 of the drive element 23 (which has a larger height than the other pin 232) can engage. When placing the breaker module 3 on the drive arrangement 2 by approaching the drive arrangement 2 in an insertion direction I (see FIG. 1), the pin 231 is introduced into the groove 310 which is easily possible if the movable part 31 is held in a predefined, central position by means of the actuation members 32A, 32B (assuming that the drive element 23 assumes a default position when no breaker module 3 is arranged on the drive arrangement 2). The coupling between the drive element 23 and the movable part 31 of the breaker module 3 hence can easily be established by holding the movable part 31 in a predefined, central position by means of the actuation members 32A, 32B.

When placing the breaker module 3 on the drive arrangement 2, the breaker module 3 is approached towards the locking elements 22A, 22B arranged on the mounting element 21 of the drive arrangement 2, and the locking elements 22A, 22B are inserted into openings 302A, 302B on the bottom face of the housing 30 and are introduced into openings 303A, 303B inside the housing 30 through engagement openings 321 of the actuation members 32A, 32B. If the actuation members 32A, 32B are in their first, inner position when placing the breaker module 3 on the drive arrangement 2, the openings 303A, 303B inside the housing 30 are accessible such that the locking elements 22A, 22B may be inserted into such openings 303A, 303B.

Once the breaker module 3 is placed on the drive arrangement 2, the actuation members 32A, 32B are released such that, due to the pretensioning force of spring elements acting between the actuation members 32A, 32B and the housing 30, they are reverted to their second position. By this a rim extending (half-way) around the engagement opening 321 of each actuation member 32A, 32B engages with the groove 220 of the corresponding locking element 22A, 22B, such that the breaker module 3 is mechanically locked to the locking elements 22A, 22B. In particular, the breaker module 3 in this way is held on the drive arrangement 2 and cannot be removed, at least not without releasing the locking, from the drive arrangement 2.

If a tubing 4 shall be opened by acting onto a closure element 40 placed within the tubing 4, the tubing 4 is inserted into the insertion direction I into a space between housing elements 301 on the housing 30 and is introduced into the reception opening 316 of the breaking element 315. During operation the drive element 23 is then rotated and moves within a space confined between protrusions 311, 312 on the movable part 31. Due to the engagement of the pin 231 with the groove 310 the movable part 31 is forced by the rotating movement of the drive element 23 into a longitudinal back and forth movement within the opening 300 of the housing 30, which is transferred to the breaking element 315 such that the breaking element 315 moves for example along a movement direction M and by this acts onto the tubing 4 placed in the reception opening 316 of the fork-shaped breaking element 315.

If the breaker module 3 shall be replaced by another breaker module 3 for acting onto a different tubing 4 comprising a different closure element 40 of a different kind, a user presses onto the actuation members 32A, 32B and by this releases the mechanical locking of the actuation members 32A, 32B and the locking elements 22A, 22B. The breaker module 3 hence may be removed from the locking elements 22A, 22B in a direction opposite the insertion direction I, and another breaker module 3 may be placed on the drive arrangement 2.

Different breaker modules 3 may comprise different movable parts 31 performing different motions. In each case, herein, a rotating movement of the drive element 23 is transferred to a corresponding movable part 31 of a breaker module 3 and by this a breaking element 315 of the breaker module 3 is driven to act onto a closure element 40 of a tubing 4 inserted into a reception opening 316 of the breaking element 315.

Once a breaker module 3 of a particular design is placed on the drive arrangement 2, the drive arrangement 2 must know in what way to drive the drive element 23 in order to move the movable part 31 along its associated movement path within the opening 300. The operation of the electric drive device 20 herein is controlled by means of a control device 5 which is constituted to energize the electric drive device 20 in order to drive the drive element 23.

In order to recognize what type of breaker module 3 has been arranged on the drive arrangement 2, the control device 5 is constituted to perform a detection routine by means of which the breaker module 3 can be identified and assigned to a particular, predefined type. During the detection routine, the control device 5 energizes the electric drive device 20 such that the drive element 23 is driven to move the movable part 31 of the breaker module 3. During the detection routine the control device 5 receives different feedback signals from different detection devices 50, 51, which may be analysed in order to derive information about the type of breaker module 3 attached to the drive arrangement 2.

A first detection device 50 herein is constituted to monitor the motor current of the electric drive device 20. A second detection device 51 may be constituted as a (micro-) mechanical switch for interacting with the movable part 31, for example with the protrusion element 311 of the movable part 31, such that by means of the mechanical switch 51 it may be recognized over which movement path the movable part 31 is moved.

In addition to the mechanical switch 51 another, second mechanical switch may be present at the other side of the drive element 23 for detecting a movement of the movable part 31 in the other driving direction.

By means of the first detection device 50 the motor current of the electric drive device 20 is monitored during the detection routine. By monitoring the motor current it can in particular be observed whether the movable part 31 abuts a stop 304, 305 within the opening 300 of the housing 30 such that a further movement of the movable part 31 beyond the stop 304, 305 is not possible. The abutment of a stop 304, 305 will cause the motor current to rise, which can be detected.

In this regard it is to be noted that by the monitoring of the motor current in principle also a position detection of the position of the movable part 31 is possible. The rotation of a rotor of the electric drive device 20 will generally cause ripples in the motor current, which in principle can be counted to determine the position.

By means of the second detection device 51 in the shape of a mechanical switch it can be observed whether the movable part 31 has reached a predefined position corresponding to the position of the mechanical switch 51. If the movable part 31, for example via its protruding element 311, interacts with the mechanical switch 51, an electrical signal is issued and fed to the control device 5.

From signals received from the detection device 50 monitoring the motor current and from the detection device 51 in the shape of a mechanical switch it is also possible to derive timing information, e.g. a time required to move the movable part 31 from one stop 304 to another stop 305. The timing indicates the length of the movement path and hence represents a characteristic information useful for identifying the type of breaker module 3.

The control device 5 is constituted to analyse the feedback signals it receives during the detection routine. Herein, different breaker modules 3 will differ in the feedback signals that are produced during the detection routine, such that from the feedback signals the breaker modules 3 attached to the drive arrangement 2 can be distinguished.

By means of the analysis of the feedback signals it hence becomes possible to identify the type of breaker module 3 attached to the drive arrangement 2. According to the type of breaker module 3 attached to the drive arrangement 2 the control device 5 can then choose a suitable movement routine for the normal operation such that the electric drive device 20 is driven in a suitable manner for moving the movable part 31 for acting onto a closure element 40 of a tubing 4.

The invention is not limited to the embodiments described above, but may be implemented in an entirely different fashion.

In particular, the breaker module may have a different shape and function. For example, the movable part may perform a rotating or swiveling movement or the like.

The breaking element of the breaker module may be fixedly connected to the movable part such that the breaking element performs the same movement as the movable part. However, it is also conceivable that the breaking element is connected to the movable part via a suitable gearing such that the movement of the movable part is transferred into a different movement of the breaking element.

LIST OF REFERENCE NUMERALS

1 Breaker device
2 Drive arrangement (backend)
20 Electric drive device
21 Mounting element
22A, 22B Lock element
220 Groove
23 Drive element
230 Body
231, 232 Pin
24 Housing element
240 Opening
3 Breaker module
30 Housing
300 Guide opening
301 Housing elements
302A, 302B Opening
303A, 303B Opening
304, 305 Stop
31 Movable part
310 Groove
311, 312 Protrusion element
313, 314 Engagement section
315 Breaking element
316 Reception opening
32A, 32B Actuation member (button)
320 Head section
321 Engagement opening
4 Tubing
40 Closure element
5 Control device
50 Detection device (motor current sensing)
51 Detection device (micromechanical switch)
D Axis of rotation
I Insertion direction
M Movement direction
P Pushing direction
R Rotation direction

The invention claimed is:

1. A breaker device for acting onto a closure element of a medical tubing, comprising:
   a drive arrangement having an electric drive device and a drive element driven by the drive device,
   a breaker module which is arrangeable on the drive arrangement, the breaker module comprising a housing, a movable part movably arranged on the housing and a breaking element for acting onto the closure element of the tubing, wherein the breaker module in an attached state is placed on the drive arrangement, the drive element being in operative connection with the movable part in the attached state such that a movement of the drive element causes the movable part to move for actuating the breaking element, and
   a control device for controlling the electric drive device for driving the drive element,
   wherein the control device is constituted to control, during a detection routine, the electric drive device to drive the drive element in order to move the movable part, and wherein the control device is further constituted to analyse at least one feedback signal received during the detection routine for determining a type of the breaker module, the feedback signal being indicative of a movement of the movable part during the detection routine.

2. The breaker device according to claim 1, wherein the drive arrangement comprises at least one detection device for providing the feedback signal in dependence of a movement of the movable part.

3. The breaker device according to claim 2, wherein the detection device is constituted to monitor a motor current of the electric drive device.

4. The breaker device according to claim 2, wherein the detection device is a mechanical switch constituted to interact with the movable part during the movement of the movable part.

5. The breaker device according to claim 4, wherein the detection device in the shape of the mechanical switch is actuated if the movable part is in a predefined position with respect to the housing.

6. The breaker device according to claim 1, wherein drive element is rotatable about an axis of rotation.

7. The breaker device according to claim 1, wherein the drive element comprises at least one coupling element to establish a positive-locking coupling with the movable part in the attached state.

8. The breaker device according to claim 1, wherein the movable part is guided on the housing such that the movable part is displaceable with respect to the housing along a longitudinal movement direction.

9. The breaker device according to claim 1, wherein the movable part, when moved by the drive element interacts with at least one stop limiting the movement of the movable part in at least one direction.

10. The breaker device according to claim 1, wherein depending on the type of the breaker module determined during the detection routine, the control device is constituted to control the electric drive device according to a particular predefined movement routine chosen from a multiplicity of different movement routines for moving the movable part in order to act onto a closure element of a tubing.

11. A method for operating a breaker device for acting onto a closure element of a medical tubing, the method comprising:
   arranging a breaker module on a drive arrangement, the breaker module comprising a housing, a movable part movably arranged on the housing and a breaking element for acting onto the closure element of the tubing, wherein by arranging the breaker module on the drive arrangement the movable part is brought into operative connection with a drive element of the drive arrangement such that a movement of the drive element causes the movable part to move for actuating the breaking element, and
   a control device controls an electric drive device of the drive arrangement for driving the drive element,
   wherein the control device controls, during a detection routine, the electric drive device to drive the drive element in order to move the movable part, wherein the control device further analyzes at least one feedback signal received during the detection routine for determining a type of the breaker module, the feedback signal being indicative of a movement of the movable part during the detection routine.

12. The breaker device according to claim 2, wherein drive element is rotatable about an axis of rotation.

13. The breaker device according to claim 3, wherein drive element is rotatable about an axis of rotation.

14. The breaker device according to claim 4, wherein drive element is rotatable about an axis of rotation.

15. The breaker device according to claim 5, wherein drive element is rotatable about an axis of rotation.

16. The breaker device according to claim 2, wherein the drive element comprises at least one coupling element to establish a positive-locking coupling with the movable part in the attached state.

17. The breaker device according to claim 3, wherein the drive element comprises at least one coupling element to establish a positive-locking coupling with the movable part in the attached state.

18. The breaker device according to claim 4, wherein the drive element comprises at least one coupling element to establish a positive-locking coupling with the movable part in the attached state.

19. The breaker device according to claim 5, wherein the drive element comprises at least one coupling element to establish a positive-locking coupling with the movable part in the attached state.

20. The breaker device according to claim 6, wherein the drive element comprises at least one coupling element to establish a positive-locking coupling with the movable part in the attached state.

* * * * *